United States Patent [19]

Saville

[11] Patent Number: Plant 5,692

[45] Date of Patent: Mar. 18, 1986

[54] ROSE PLANT

[75] Inventor: F. Harmon Saville, Rowley, Mass.

[73] Assignee: Nor'East Miniature Roses, Inc., Rowley, Mass.

[21] Appl. No.: 653,351

[22] Filed: Sep. 24, 1984

[51] Int. Cl.[4] ..... A01H 5/00

[52] U.S. Cl. ..... Plt./10

[58] Field of Search ..... Plt./10

*Primary Examiner*—Robert E. Bagwill

*Attorney, Agent, or Firm*—Vincent G. Gioia

[57] ABSTRACT

A new miniature rose variety of bright red flower coloring and of exhibition form.

1 Drawing Figure

1

The present invention relates to a new and distinct variety of rose plant of the miniature rose class, which was originated by my crossing as seed and pollen parents two unnamed, unpatented seedlings of my creation. The varietal denomination of this new variety is "Savapiece".

Among the novel characteristics possessed by this new variety which distinguish if from its parents and all other varieties of which I am aware are its bright red flowers of exhibition form with good to heavy petalage and which maintain its color and form. Flowers are long lasting on the plant and as cut flowers. Asexual reproduction by budding of the new variety as performed in Essex County, Mass., shows that the foregoing and other distinguishing characteristics come true to form and are established and transmitted through succeeding propagations.

The accompanying drawings show typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "45A" is plate 45A of The Royal Horticultural Society Colour Chart.

Parentage: Seedling.

*Seed parent.*—Unnamed seedling.

*Pollen parent.*—Unnamed seedling.

Class: Miniature.

The following observations are made of specimens grown outdoors in Essex County, Mass., during the month of July.

1. FLOWER

Blooming habit: Near continuous.

A. Bud:

(1) *Size.*—Medium.

(2) *Form.*—Pointed, ovate.

(3) *Color.*—When sepals first divide — Near 187C. When petals begin to unfurl — Near 45A.

(4) *Sepals.*—Longer than bud, slightly foliated.

(5) *Peduncle.*—Length — About ¾ to 1 inch. Aspect — Straight. Strength — Erect. Color — Near 195A overlayed with 181C.

2

B. Bloom:

(1) *Size.*—Average size when fully expanded — About 1½ inches.

(2) *Borne.*—Singly and sprays of three to five blooms.

(3) *Form.*—High centered, becoming flat outer petals reflex sharply upon opening; flower maintains symmetrical exhibition form.

(4) *Petalage.*—Number of petals under normal conditions — About 35 to 40.

(5) *Color.*—After sepals fall, visible flower coloring is bright red 45A with very little color difference at petal top and undersurface. Color is stable and constant through exhibition stages. General tonality from a distance is similar bright red coloring aging to near 53B. Color at point of petal attachment is near 9A.

C. Petals:

(1) *Texture.*—Thick.

(2) *Appearance.*—Inside — Velvety, outside — satiny.

(3) *Form.*—Broad, fan shaped with pronounced apex on many petals.

(4) *Arrangement.*—Regularly arranged, shingle-like.

(5) *Petaloids in center.*—Few.

(6) *Persistence.*—Drop off cleanly.

(7) *Fragrance.*—None.

(8) *Lasting quality.*—Long lasting on plant and long lasting as cut flower.

2. REPRODUCTIVE ORGANS

A. Stamens, filaments and anthers:

(1) *Arrangement.*—Regularly arranged around styles.

(2) *Color.*—Near 160A.

B. Pollen:

*Color.*—Near 10B.

C. Styles: Uneven length, bunched.

D. Stigmas:

*Color.*—Near 10D.

E. Hips: None observed.

3. PLANT

A. Form: Bushy, Compact.

B. Growth: Vigorous.

*Height attained.*—About 12 to 15 inches.

C. Foliage: Compound 5 to 7 leaflets.

(1) *Size.*—Medium.

(2) *Quantity.*—Abundant.

(3) *Color.*—New foliage: Upper side — Near to 146A. Under side — Near to 148C. Old foliage: Upper side — Near 137A. Under side — Near 148B.

(4) *Shape.*—Oval.

(5) *Texture.*—Upper side is waxy and under side is matte.

(6) *Edge.— Serrated.*

(7) *Serration.*—Serrulate.

(8) *Leaf stem.*—Color — Reddish brown. Under side — Near 146B.

(9) *Stipules.*—Medium.

(10) *Resistance to disease.*—Blackspot — Average. Mildew — Average. Rust — Average.

D. Wood:

(1) *New Wood.*—Color — Near 59A. Bark — Smooth.

(2) *Old wood.*—Color — Near 146B. Bark — Smooth.

E. Thorns:

(1) *Thorns.*—Quantity (main stalk): Ordinary. On laterals from stalk — Few. Form — Curving sharply downward. Length — Medium. Color — Near 182A. Position — Irregular.

(2) *Prickles.*—Few.

F. Winter hardiness: Requires ordinary protection in extreme climates.

I claim:

1. A new and distinct variety of rose plant of the miniature rose class, substantially as shown and described, characterized particularly by bright red flowers of exhibition form and medium to heavy petalage with outer petals reflexing sharply upon opening and good color stability.

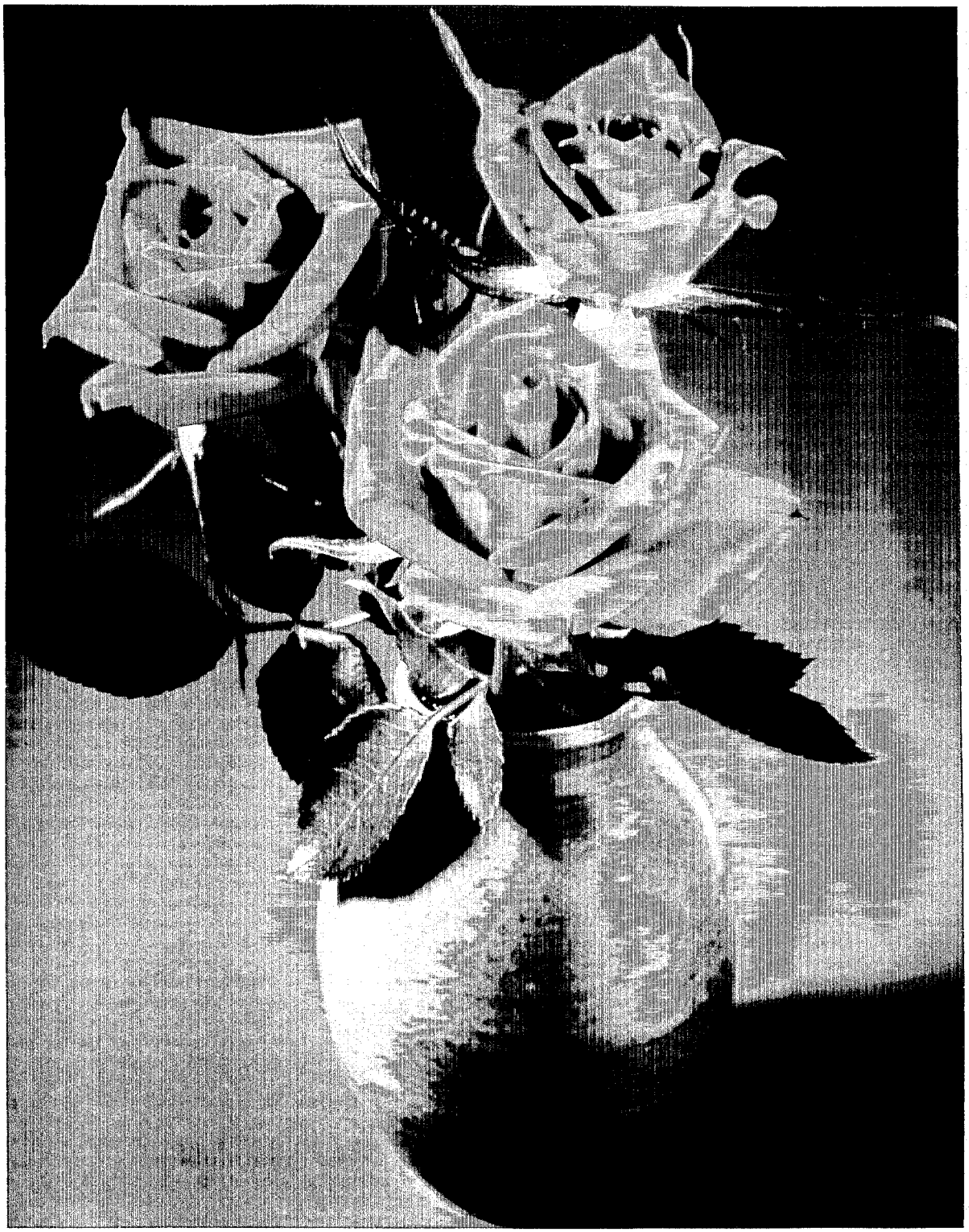

* * * * *